United States Patent
Berge

(10) Patent No.: US 7,806,286 B2
(45) Date of Patent: Oct. 5, 2010

(54) PUSH/POP CLOSURE

(75) Inventor: Gary L. Berge, Crystal Lake, IL (US)

(73) Assignee: Rexam Consumer Plastics, Inc., Pittsburgh, PA (US)

( * ) Notice: Subject to any disclaimer, the term of this patent is extended or adjusted under 35 U.S.C. 154(b) by 372 days.

(21) Appl. No.: 12/080,922

(22) Filed: Apr. 7, 2008

(65) Prior Publication Data

US 2008/0245797 A1     Oct. 9, 2008

Related U.S. Application Data

(60) Provisional application No. 60/922,207, filed on Apr. 6, 2007.

(51) Int. Cl.
*B65D 43/04*     (2006.01)
*B65D 51/12*     (2006.01)

(52) U.S. Cl. .................... 220/282; 220/506; 220/305; 43/131

(58) Field of Classification Search ............... 220/281, 220/282, 305, 506, 526; 215/211, 215; 43/131, 43/132.1
See application file for complete search history.

(56) References Cited

U.S. PATENT DOCUMENTS

| | | | | |
|---|---|---|---|---|
| 5,901,496 A | * | 5/1999 | Woodruff | 43/124 |
| 5,953,854 A | | 9/1999 | Hyatt | |
| 6,003,266 A | * | 12/1999 | Woodruff | 43/124 |
| 6,065,241 A | * | 5/2000 | Woodruff | 43/132.1 |

* cited by examiner

*Primary Examiner*—Harry A Grosso
(74) *Attorney, Agent, or Firm*—Chad D. Bruggeman; John F. Salazar; Middleton Reutlinger

(57) ABSTRACT

A closure device and methods for manufacturing closure a device having a lid that is capable of alternating convex-to-concave movement and concave-to-convex movement. The lid may be mounted to a closure body, which may, for example, contain substances for attracting and exterminating pests, such as ants, other insects, snakes, and rodents. In other embodiments, the closure body may contain other substances, for example, a vaporizable air freshener. Certain embodiments may include a stake for affixing the closure body to the ground.

27 Claims, 5 Drawing Sheets

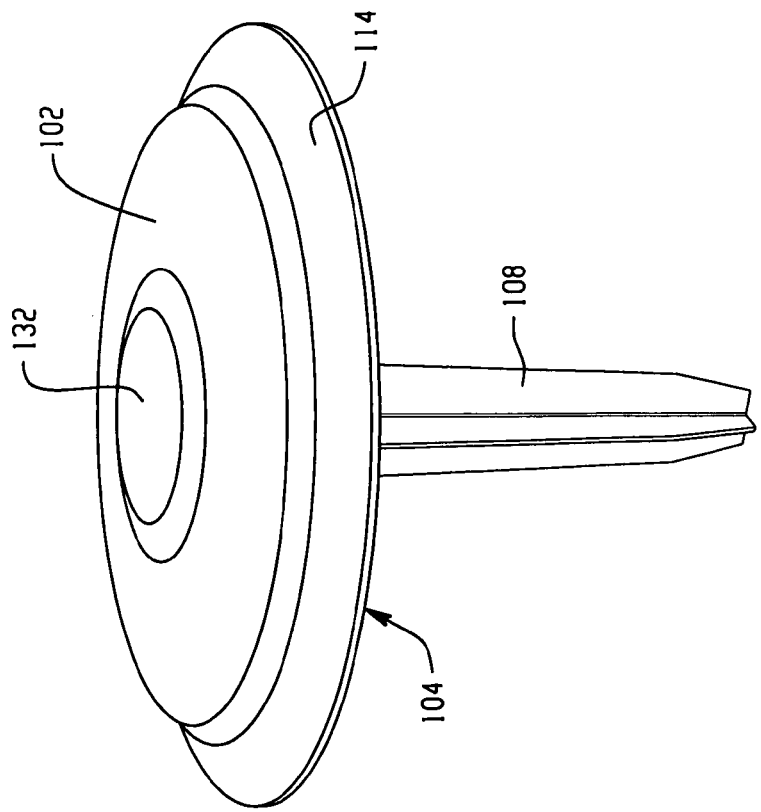
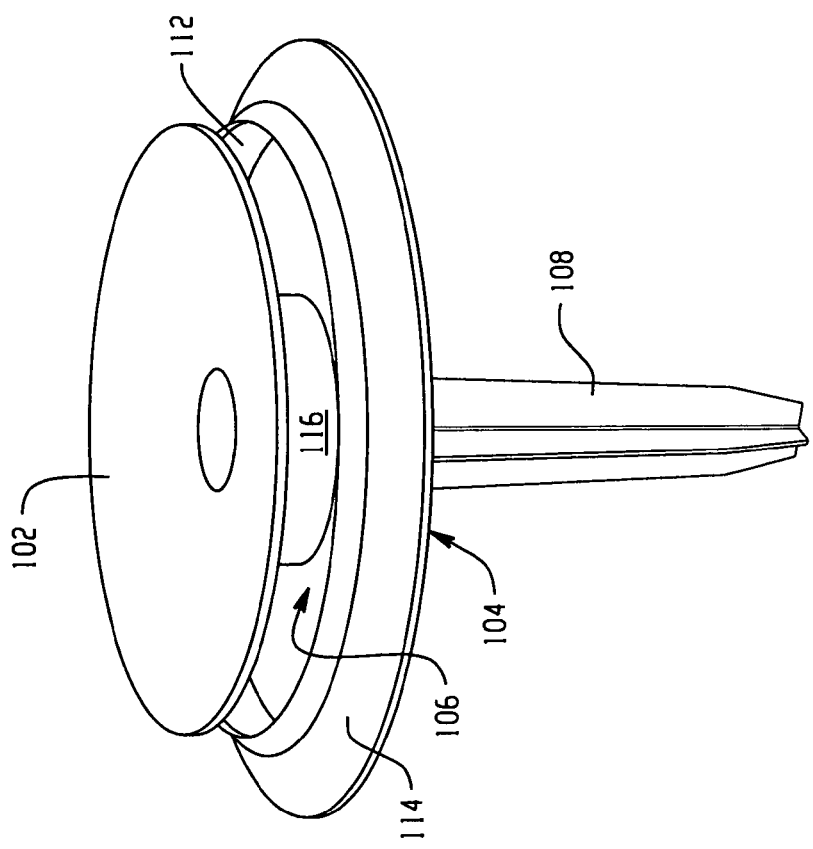

PUSH/POP CLOSURE

CROSS REFERENCE TO RELATED APPLICATION

This application claims the benefit of U.S. Provisional Application No. 60/922,207, filed Apr. 6, 2007, which is hereby incorporated by reference in its entirety.

BACKGROUND OF THE INVENTION

1. Field of the Invention

The present invention is directed to closures and associated methods of fabricating closures and, more specifically, to push/pop closures that may be adapted for use in pest control or as air fresheners, as well as methods of fabricating push/pop closures.

2. Description of the Related Art

Pest control devices and conventional air fresheners may include a container holding a substance that is adapted to be selectively exposed to the surrounding environment. For example, a pest control device may contain an insect bait and an air freshener may contain a volatile air-freshening substance.

INTRODUCTION TO THE INVENTION

Embodiments of the invention are directed to a closure device and methods for manufacturing closure a device having a lid that is capable of alternating convex-to-concave movement and concave-to-convex movement. The lid may be mounted to a closure body, which may, for example, contain substances for attracting and exterminating pests, such as ants, other insects, snakes, and rodents. In other embodiments, the closure body may contain other substances, for example, a vaporizable air freshener. Certain embodiments may include a stake for affixing the closure body to the ground.

In a first aspect, a container according to the present invention may include a base including a floor, a first continuous wall extending from the floor, a first projection extending from the floor and circumscribed by the first continuous wall, and a second projection extending from the floor between the first continuous wall and the first projection; and a lid mounted movably to the base, the lid including a first ceiling section including a first appendage extending from an interior surface of the first ceiling section; a second ceiling section circumscribing the first ceiling section; wherein the first projection slidably engages the first appendage to movably mount the lid to the base; and wherein the lid is movable between a concave open position and a convex closed position.

In a detailed embodiment of the first aspect, the first projection may be a generally cylindrically shaped wall, and the second projection may be a generally cylindrically shaped wall circumscribing the first projection.

In another detailed embodiment of the first aspect, a height of the first projection may be less than a height of the second projection, and the lid may be mounted to the first continuous wall, the first projection, and the second projection in the convex position; and the lid may be mounted to only the first projection and the second projection in the concave position. The lid may include a third projection interacting with the first projection to retain the lateral position of the lid with respect to the base in both the convex closed position and the concave open position; and the lid may include a flange interposing the first ceiling section and the second ceiling section, and the flange may interface with the second projection.

In yet another detailed embodiment of the first aspect, the container may further include a ground stake mounted to the base for retaining the container in a fixed position.

In yet another detailed embodiment of the first aspect, the container may include at least one of an animal bait and a vaporizable air freshener located within the base.

In a second aspect, a container according to the present invention may include a base including a bottom wall, a first continuous wall extending generally perpendicularly from the bottom wall, a second wall extending generally perpendicularly from the bottom wall, the second wall being circumscribed by the first continuous wall, where an interior of the first continuous wall and an exterior of the second wall at least partially define a first well, and a third wall extending generally perpendicularly from the bottom wall, the third wall being substantially circumscribed by the second wall; and a lid mounted movably to the base, the lid including an inner dome section including a first projection extending from an interior surface, the inner dome section being outlined by a second projection also extending from the interior surface; and an outer dome section extending from the inner dome section to an outer boundary; wherein the first projection slidably engages the third wall to movably mount the lid to the base. The lid may be movable between a concave open position and a convex closed position, the second projection may selectively engage the first continuous wall when the lid is in the closed position, and, when the lid is in the concave open position, the first well may be accessible from an exterior of the container and, when the lid is in the convex closed position, the first well may not be accessible from the exterior of the container.

In a detailed embodiment of the second aspect, in the convex closed position, the second projection may releasably engage the first continuous wall of the base and, in the concave open position, the second projection may be vertically spaced apart from the first continuous wall of the base. The container may include a downwardly extending stake mounted to the bottom wall for retaining the container in a fixed location. The first projection may be a cylinder extending from the lid which extends into a cavity defined by an interior surface of the third wall and the first projection may be slidably engaged with the interior surface of the third wall. The second wall may have a height greater than a height of the third wall. The base may further include a circumferential flange mounted to and extending radially beyond the first continuous wall.

In another detailed embodiment of the second aspect, the bottom wall, the first continuous wall, the second wall, and the third wall may be formed as a first unitary body.

In yet another detailed embodiment of the second aspect, the inner dome section, the outer dome section, the first projection, and the second projection are formed as a second unitary body.

In yet another detailed embodiment of the second aspect, the first well may contain at least one of a pest bait and a vaporizable air freshener.

In a third aspect, a method of fabricating a container according to the present invention may include the steps of providing a base, the base including a bottom wall and a plurality of upwardly extending walls, at least two of the plurality of walls and the bottom wall at least partially defining a well; loading the well with a payload; providing a lid, the lid including an inner dome section and an outer dome section, the inner dome section including a projection, wherein the inner dome section and the outer dome section cooperate to snap between a convex configuration and a concave configuration; and coupling the lid to the base by slidably engaging the projection with at least one of the plurality of walls. The well may be accessible when the lid is in the concave configuration and the well may not be accessible when the lid is in the convex configuration.

In a detailed embodiment of the third aspect, the step of providing the base may include the step of injection molding the base and the step of providing the lid may include the step of injection molding the lid. The step of loading the well may include the step of placing at least one of a pest bait and a vaporizable air freshener in the well.

In another detailed embodiment of the third aspect, the base may include a ground stake mounted to the bottom wall and extending downwardly away from the base for retaining the base in a fixed position.

In yet another detailed embodiment of the third aspect, the base may include a first wall, a second wall, and a third wall, the first wall circumscribing the second wall and the second wall circumscribing the third wall. The projection may slidably engage the third wall, the lid may releasably engage the first wall in the convex configuration, and the lid may not engage the first wall in the concave configuration. The second wall may have a height greater than the height of the third wall and the second wall may act as a fulcrum when snapping the lid between the convex configuration and the concave configuration.

In a fourth aspect, a container according to the present invention may include a base; and a domed lid, of a generally flexible and resilient material, engaged with the base at a hub of the lid so as to be vertically moveable, up and down, with respect to the base at the hub of the lid. The base may include a fulcrum projecting radially upward therefrom towards the lid, the fulcrum projection being positioned radially outside of the hub of the lid. Downward force on the hub of the lid may cause the lid to engage the fulcrum projection radially outside of the hub of the lid and invert the domed lid to a cupped lid, thereby providing a radially accessible opening to the container radially outside of the fulcrum. Downward force on the cupped lid radially outside the fulcrum may cause the lid to engage the fulcrum and revert the cupped lid back to a domed lid, thereby closing the opening to the container.

In a detailed embodiment of the third aspect, the domed lid may be in sliding engagement with the base.

In another detailed embodiment of the third aspect, the domed lid may include a projection extending from the lid towards the base, the base may include a generally cylindrical wall extending towards the lid, and the projection and the generally cylindrical wall may be slidably engaged.

In yet another detailed embodiment of the third aspect, the fulcrum may be a generally cylindrical wall projecting upwards from the base towards the lid.

In yet another detailed embodiment of the third aspect, the container may include an outer wall projecting from the base approximate the outer periphery of the lid, thereby providing a storage chamber between the fulcrum and the outer wall.

In yet another detailed embodiment of the third aspect, the base may be constructed from a substantially rigid material.

BRIEF DESCRIPTION OF THE SEVERAL VIEWS OF THE DRAWINGS

FIG. 3 is a perspective view the first exemplary closure, in the open position;

FIG. 4 is a perspective view the first exemplary closure, in the closed position;

DETAILED DESCRIPTION OF THE INVENTION

The exemplary embodiments of the present invention are described and illustrated below to encompass push/pop closures, as well as methods of fabricating push/pop closures. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 1:
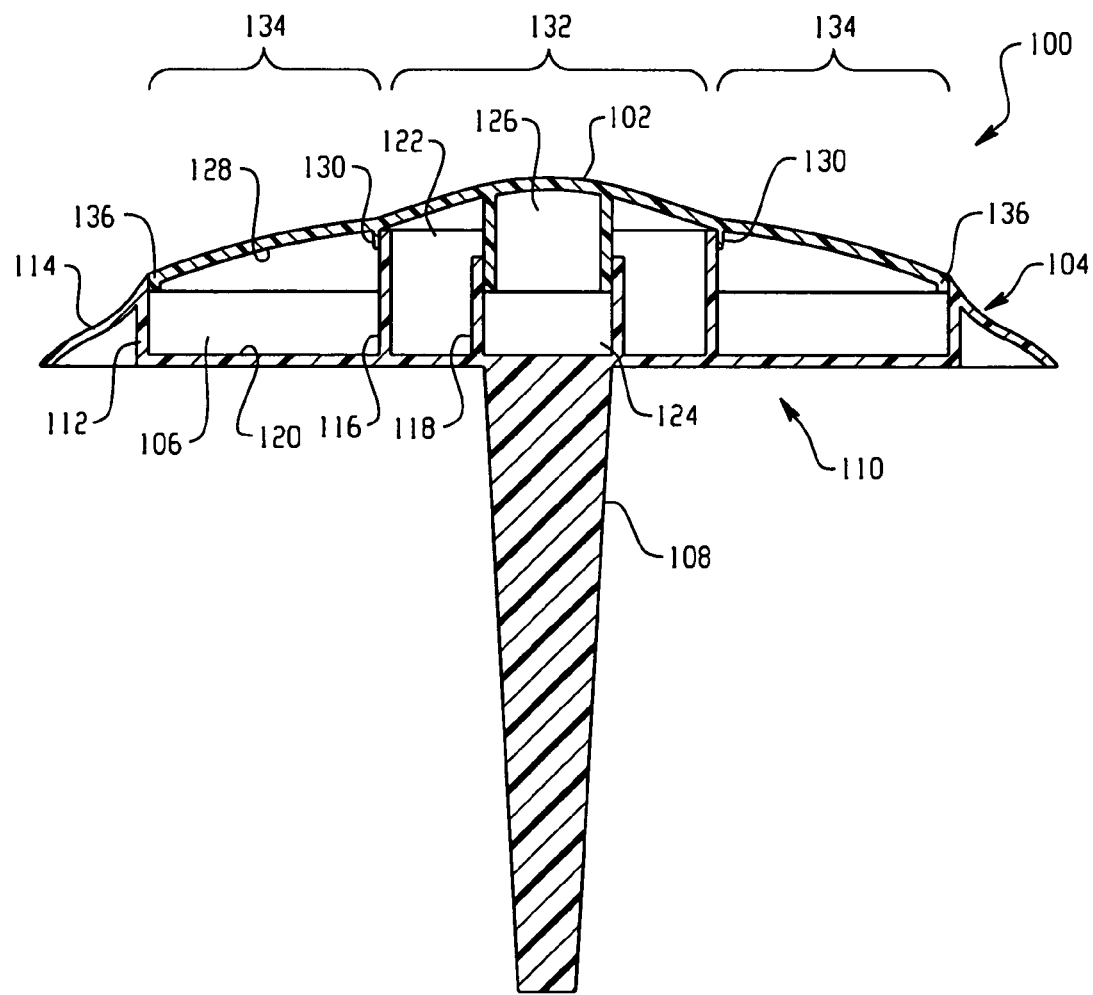
FIG. 1 is a cross-sectional view of a first exemplary closure, in the closed position.
Figure 2:
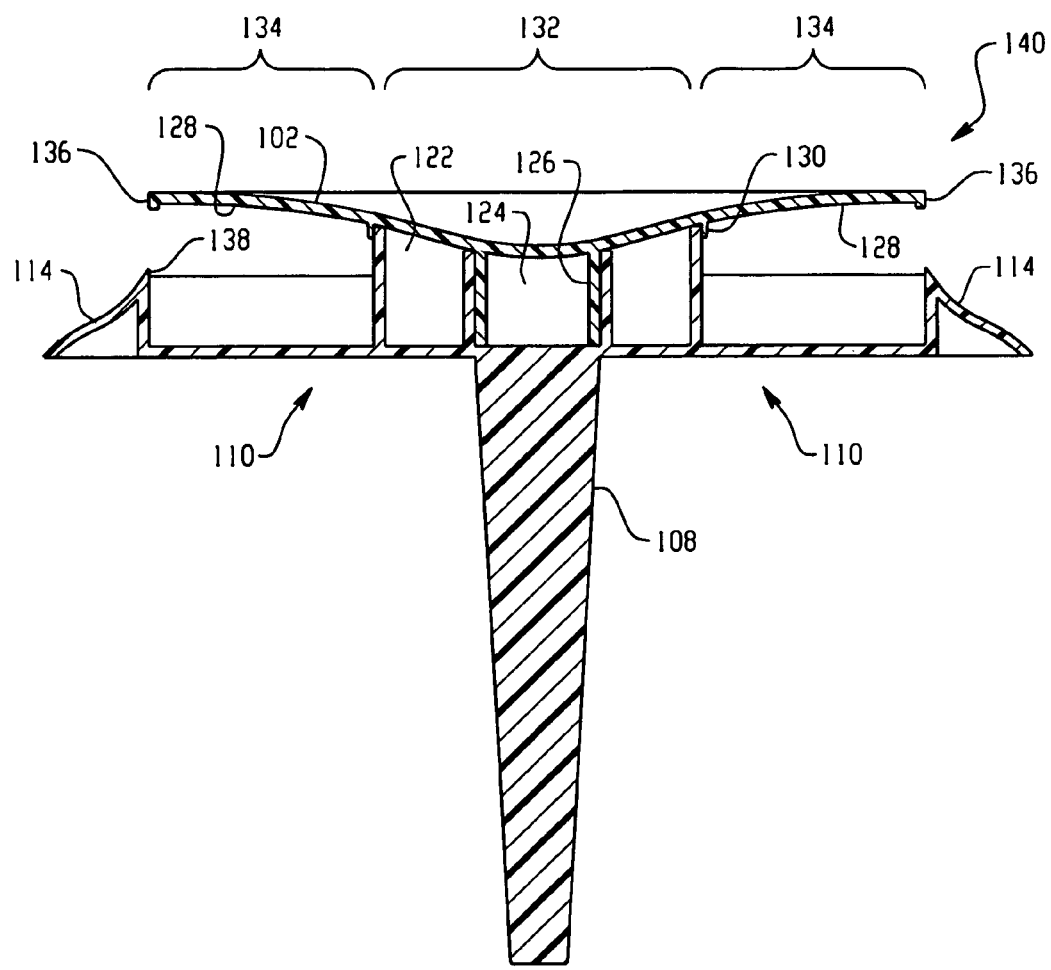
FIG. 2 is a cross-sectional view of the first exemplary closure, in the open position.
Figure 5:
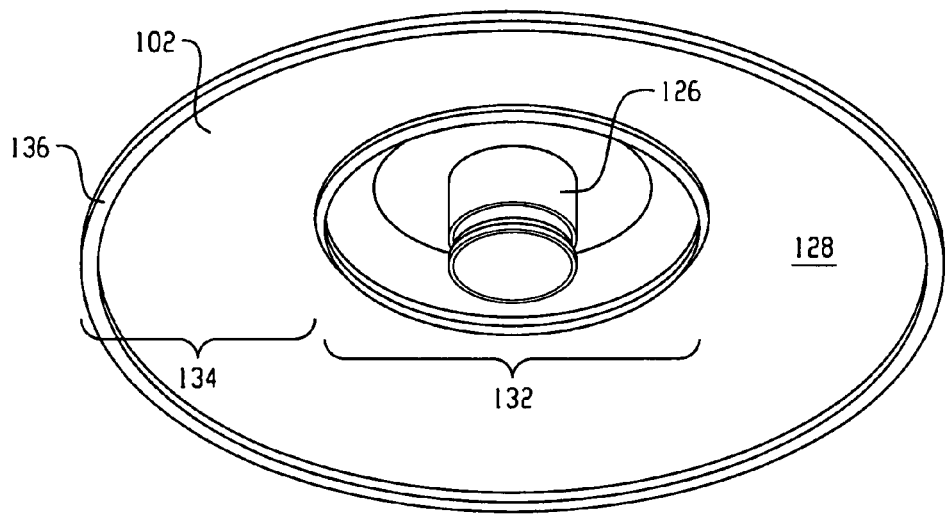
FIG. 5 is an underneath perspective view of an exemplary repositionable cap of the first exemplary closure.
Figure 6:
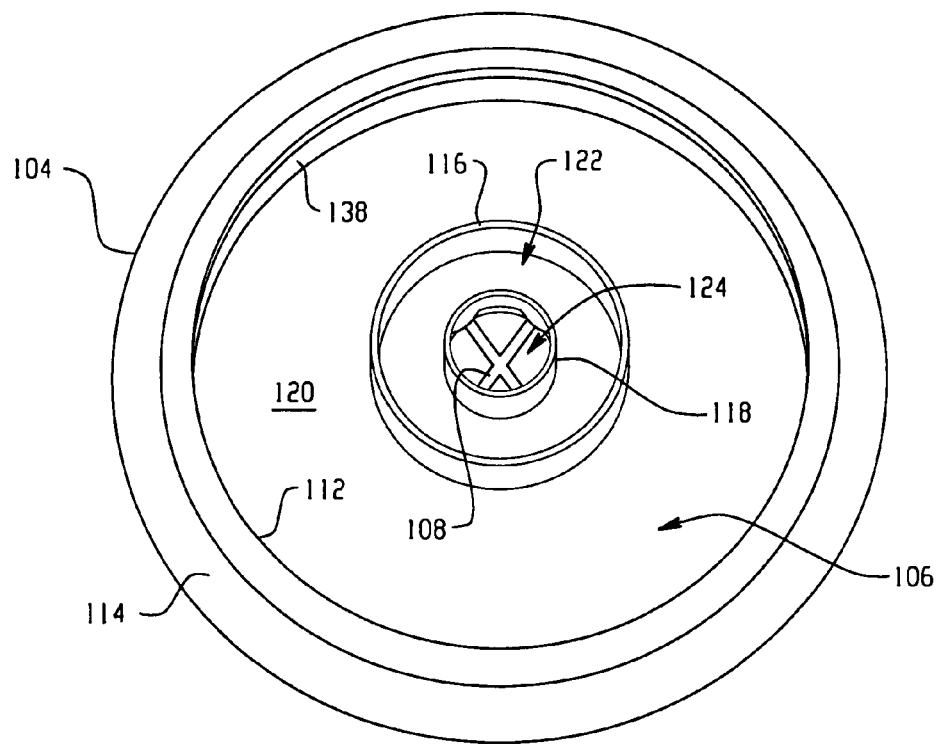
FIG. 6 is an elevated perspective view of an exemplary base of the first exemplary closure.
Figure 7:
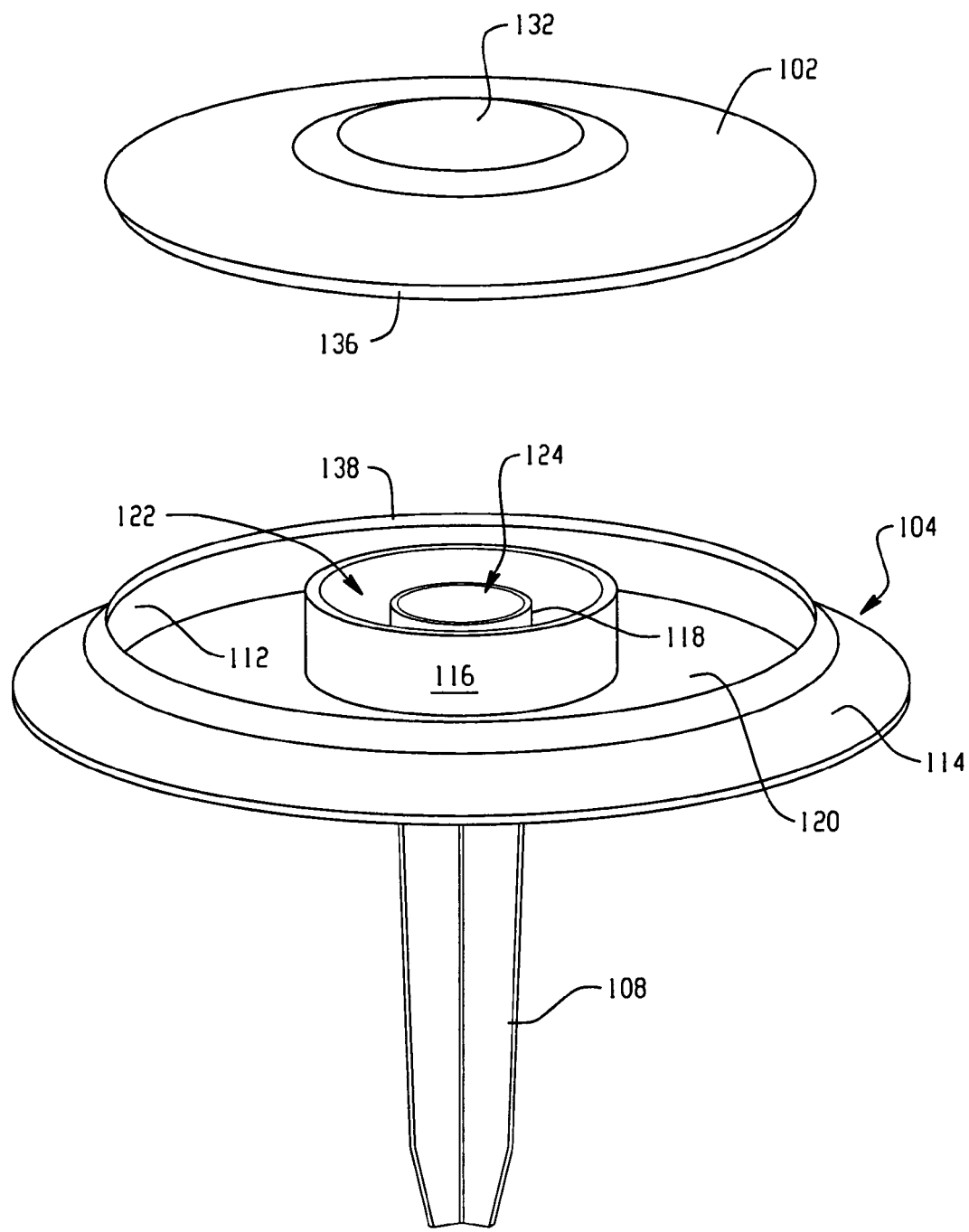
FIG. 7 is an exploded view of the first exemplary closure.

Referencing FIGS. 1-7, an exemplary push/pop closure 100 is generally circular in footprint and includes an injection molded lid 102 repositionably mounted to a base 104 in order to selectively open or close off a circumferential bait well 106. For purposes of explanation, and not limitation, the exemplary push/pop closure 100 will be discussed in one of its many applications as a pest trap 100. It is to be understood that the exemplary pest trap 100 is operative to attract and exterminate pests such as, without limitation, insects, rodents, and snakes. However, the exemplary push/pop closure is also amendable to deodorizer and air freshener applications, where a vaporizable air freshener may be used in lieu of a pest bait.

The exemplary circular insect trap 100 may be adapted for use indoors or outdoors. When utilized for outdoor use, the trap 100 may include a stake 108 which may to be driven into the ground in order to secure the trap in a particular location. The stake 108 may be an integral projection from the base 104. However, it is also within the scope of the invention for the trap 100 to include a removable stake 108, thus rendering the trap amendable to both indoor and outdoor applications.

The base 104 of the trap 100 comprises an molded platform having a generally planar underside 110 that is well suited to mount the trap to generally planar surfaces, such as the floor of a building. The base 104 also includes an outermost circumferential wall 112 that is generally perpendicular to the underside 110. A circumferential flange 114 extends away from the interior of the base 104 and is operative to form a ramp allowing pests to travel up the flange and into the bait well 106. The height of the outermost circumferential wall 112 and the circumferential flange may vary depending upon the pest targeted for extermination, however, those skilled in the art will understand that the wall 112 is of sufficient height to retain pest bait within the trap 100. In other exemplary embodiments, a wall supplementing or in lieu of outermost circumferential wall 112 may be mounted to the lid 102. Positioned radially within the outermost circumferential wall 112 is a concentric second circular wall 116, and radially within the second wall 116 is a third concentric circular wall 118.

The second circular wall 116 and the third circular wall 118 are dimensioned to allow repositioning of the lid 102 between an open position (i.e., a concave position) and a closed position (i.e., a convex position). As will be described below, the second circular wall 116 acts as a fulcrum for directing the lid 102 into a concave orientation when pressure is applied to the hub of the lid 102, and for directing the lid back to the convex orientation when pressure is applied to the top of the lid radially outward from the fulcrum. In an exemplary embodiment, the second circular wall 116 has a diameter approximately twice the diameter of the third circular wall 118, while the height of the third circular wall 118 is approximately 20% less than the height of the second circular wall 116. Each of the circular walls 116, 118 cooperates with the floor 120 to respectively define cylindrical cavities 122, 124. The second, inner cylindrical cavity 124 receives a cylindrical projection 126 that extends downward from the interior side 128 (the bottom surface) of the lid 102 at the hub. The interior side 128 of the lid 102 also includes a raised circular wall 130 that circumscribes the first circular wall 116 to establish a compression fit between the walls 116, 130 in order to mount the lid 102 to the base 104. The lid 102 is generally dome-shaped and includes an inner dome section 132 and a more gradually sloped outer dome section 134. Finally, the lid 102 includes a downwardly extending circumferential collar 136 that abuts a shoulder 138 on the outermost circumferential wall 112 and forms a compression fit between the lid 102 and base 104, also to retain the lid 102 in the closed position, until the lid it repositioned open.

To reposition the lid 102 from its closed position (see FIGS. 1 and 4) to its open position (see FIGS. 2 and 3), a user depresses the inner dome 132 section (radially within the fulcrum 116) and repositions the cylindrical projection 126 toward the floor 120, thereby moving the projection 126 farther into the second cylindrical cavity 124. Continued downward pressure upon the inner dome section 132 and engagement with the fulcrum provided by the second wall 116 causes the lid 102 to invert its position (called "snapping") from a substantially convex position (see FIGS. 1 and 4) to a substantially concave position (see FIGS. 2 and 3). The concave position of the outermost dome section 134 is operative to space apart the collar 136 from the shoulder 138, thereby creating an annular opening allowing access from the exterior of the trap 100 to the bait well 106.

To reposition the lid 102 from its open position to its closed position, a user depresses the outermost dome section 134 and repositions the collar 136 toward the shoulder 138, thereby decreasing the height of the annular opening. Upon continued movement of the collar 136 toward the shoulder 138, engagement with the fulcrum provided by the second wall 116 causes the lid 102 to snap back from a concave position to a convex position so that the collar abuts the shoulder. As the lid 102 is repositioned, the projection 126 is also repositioned. In the exemplary embodiment, the projection 126 traverses from a position where a substantial portion of the projection is located within the cylindrical cavity 124 to a position where less than half of the projection is located within the cylindrical cavity.

Each of the foregoing major components, the base 104 and lid 102, may be injection molded and thereafter assembled. Assembly of the base 104 and 102 lid is usually carried out after either or both have been baited, with the base and lid being mounted to one another to retain the bait within the trap 100.

The base 104 and lid 102 may be constructed from any suitable materials. In certain exemplary embodiments, the base 104 may be constructed from a substantially rigid material. The lid 102 may be constructed from a somewhat flexible and resilient material to permit inversion between convex and concave shapes. Further, the lid 102 may be constructed from a material having appropriate fatigue characteristics to permit repeated inversion of the lid between the convex and concave shapes without failure.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A container comprising:
    a base including
        a floor,
        a first continuous wall extending from the floor,
        a first projection extending from the floor and circumscribed by the first continuous wall, and
        a second projection extending from the floor between the first continuous wall and the first projection; and
    a lid mounted movably to the base, the lid including
        a first ceiling section including a first appendage extending from an interior surface of the first ceiling section;
        a second ceiling section circumscribing the first ceiling section;
    wherein the first projection slidably engages the first appendage to movably mount the lid to the base; and
    wherein the lid is movable between a concave open position and a convex closed position.

2. The container of claim 1, wherein the first projection is a generally cylindrically shaped wall, and the second projection is a generally cylindrically shaped wall circumscribing the first projection.

3. The container of claim 1, wherein a height of the first projection is less than a height of the second projection, and wherein the lid is mounted to the first continuous wall, the first projection, and the second projection in the convex position; and
    wherein the lid is mounted to only the first projection and the second projection in the concave position.

4. The container of claim 3, wherein the lid includes a third projection interacting with the first projection to retain the lateral position of the lid with respect to the base in both the convex closed position and the concave open position; and
    wherein the lid includes a flange interposing the first ceiling section and the second ceiling section, and the flange interfaces with the second projection.

5. The container of claim 1, further comprising a ground stake mounted to the base for retaining the container in a fixed position.

6. The container of claim 1, further comprising at least one of an animal bait and a vaporizable air freshener located within the base.

7. The container of claim 1, wherein the base is constructed from a substantially rigid material.

8. A container comprising:
a base including
a bottom wall,
a first continuous wall extending generally perpendicularly from the bottom wall,
a second wall extending generally perpendicularly from the bottom wall, the second wall being circumscribed by the first continuous wall, where an interior of the first continuous wall and an exterior of the second wall at least partially define a first well, and
a third wall extending generally perpendicularly from the bottom wall, the third wall being substantially circumscribed by the second wall; and
a lid mounted movably to the base, the lid including
an inner dome section including a first projection extending from an interior surface, the inner dome section being outlined by a second projection also extending from the interior surface; and
an outer dome section extending from the inner dome section to an outer boundary;
wherein the first projection slidably engages the third wall to movably mount the lid to the base;
wherein the lid is movable between a concave open position and a convex closed position;
wherein the second projection selectively engages the first continuous wall when the lid is in the closed position; and
wherein, when the lid is in the concave open position, the first well is accessible from an exterior of the container and, when the lid is in the convex closed position, the first well is not accessible from the exterior of the container.

9. The container of claim 8, wherein, in the convex closed position, the second projection releasably engages the first continuous wall of the base and, in the concave open position, the second projection is vertically spaced apart from the first continuous wall of the base.

10. The container of claim 9, further comprising a downwardly extending stake mounted to the bottom wall for retaining the container in a fixed location.

11. The container of claim 9, wherein the first projection is a cylinder extending from the lid which extends into a cavity defined by an interior surface of the third wall; and
wherein the first projection is slidably engaged with the interior surface of the third wall.

12. The container of claim 11, wherein the second wall has a height greater than a height of the third wall.

13. The container of claim 11, wherein the base further includes a circumferential flange mounted to and extending radially beyond the first continuous wall.

14. The container of claim 8, wherein the bottom wall, the first continuous wall, the second wall, and the third wall are formed as a first unitary body.

15. The container of claim 8, wherein the inner dome section, the outer dome section, the first projection, and the second projection are formed as a second unitary body.

16. The container of claim 8, wherein the first well contains at least one of a pest bait and a vaporizable air freshener.

17. A method of fabricating a container comprising the steps of:
providing a base, the base including a bottom wall and a plurality of upwardly extending walls, at least two of the plurality of walls and the bottom wall at least partially defining a well;
loading the well with a payload;
providing a lid, the lid including an inner dome section and an outer dome section, the inner dome section including a projection, wherein the inner dome section and the outer dome section cooperate to snap between a convex configuration and a concave configuration; and
coupling the lid to the base by slidably engaging the projection with at least one of the plurality of walls;
wherein the well is accessible when the lid is in the concave configuration and the well is not accessible when the lid is in the convex configuration.

18. The method of claim 17, wherein the step of providing the base includes the step of injection molding the base; and
wherein the step of providing the lid includes the step of injection molding the lid.

19. The method of claim 18, wherein the step of loading the well includes the step of placing at least one of a pest bait and a vaporizable air freshener in the well.

20. The method of claim 17, wherein the base includes a ground stake mounted to the bottom wall and extending downwardly away from the base for retaining the base in a fixed position.

21. The method of claim 17, wherein the base includes a first wall, a second wall, and a third wall, the first wall circumscribing the second wall and the second wall circumscribing the third wall; and
wherein the projection slidably engages the third wall, the lid releasably engages the first wall in the convex configuration, and the lid does not engage the first wall in the concave configuration.

22. The method of claim 21, wherein the second wall has a height greater than the height of the third wall; and
wherein the second wall acts as a fulcrum when snapping the lid between the convex configuration and the concave configuration.

23. A container comprising:
a base; and
a domed lid, of a generally flexible and resilient material, engaged with the base at a hub of the lid so as to be vertically moveable, up and down, with respect to the base at the hub of the lid; wherein the domed lid is in sliding engagement with the base;
the base including a fulcrum projecting radially upward therefrom towards the lid, the fulcrum projection being positioned radially outside of the hub of the lid;
wherein downward force on the hub of the lid causes the lid to engage the fulcrum projection radially outside of the hub of the lid and invert the domed lid to a cupped lid, thereby providing a radially accessible opening to the container radially outside of the fulcrum; and
wherein downward force on the cupped lid radially outside the fulcrum causes the lid to engage the fulcrum and revert the cupped lid back to a domed lid, thereby closing the opening to the container.

24. The container of claim 23, wherein the domed lid includes a projection extending from the lid towards the base, the base includes a generally cylindrical wall extending towards the lid, and the projection and the generally cylindrical wall are slidably engaged.

25. The container of claim 23, wherein the fulcrum is a generally cylindrical wall projecting upwards from the base towards the lid.

26. The container of claim 23, further comprising an outer wall projecting from the base approximate the outer periphery of the lid, thereby providing a storage chamber between the fulcrum and the outer wall.

27. The container of claim 23, wherein the base is constructed from a substantially rigid material.

* * * * *

UNITED STATES PATENT AND TRADEMARK OFFICE
CERTIFICATE OF CORRECTION

PATENT NO. : 7,806,286 B2  
APPLICATION NO. : 12/080922  
DATED : October 5, 2010  
INVENTOR(S) : Gary L. Berge Page 1 of 1

It is certified that error appears in the above-identified patent and that said Letters Patent is hereby corrected as shown below:

On the Title Page, Item (57) Abstract, Line 1: replace "closure a" with --a closure--
Column 1, Line 30: replace "closure a" with --a closure--
Column 4, Line 39: delete "to" after "may"
Column 4, Line 45: replace "an" with --a--
Column 5, Line 24: replace "it" with --is--

Signed and Sealed this
Tenth Day of April, 2012

David J. Kappos
*Director of the United States Patent and Trademark Office*